(12) United States Patent
Kolosov et al.

(10) Patent No.: US 7,210,332 B2
(45) Date of Patent: May 1, 2007

(54) MECHANICAL RESONATOR

(75) Inventors: Oleg Kolosov, San Jose, CA (US); Leonid Matsiev, San Jose, CA (US); David Padowitz, Mountain View, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 101 days.

(21) Appl. No.: 10/804,446

(22) Filed: Mar. 19, 2004

(65) Prior Publication Data

US 2004/0244487 A1 Dec. 9, 2004

Related U.S. Application Data

(60) Provisional application No. 60/456,767, filed on Mar. 21, 2003.

(51) Int. Cl.
*G01N 29/036* (2006.01)
*G01N 9/10* (2006.01)

(52) U.S. Cl. .................... 73/24.06; 73/31.06

(58) Field of Classification Search .............. None
See application file for complete search history.

(56) References Cited

U.S. PATENT DOCUMENTS

| | | | |
|---|---|---|---|
| 3,273,377 A | 9/1966 | Testerman et al. | |
| 3,622,968 A | 11/1971 | Silverman | |
| 3,710,275 A | 1/1973 | Tanaka et al. | |
| 3,718,032 A | 2/1973 | Gray | |
| 3,762,197 A | 10/1973 | Roof et al. | |
| 3,778,757 A | 12/1973 | Houston | |
| 3,902,365 A | 9/1975 | Knauth | |
| 3,903,732 A | 9/1975 | Rork et al. | |
| 3,921,622 A | 11/1975 | Cole | |
| 3,926,271 A | 12/1975 | Patashinck | |
| 4,103,224 A | 7/1978 | Taro et al. | |
| 4,145,922 A | 3/1979 | Estrada, Jr. et al. | |
| 4,282,499 A * | 8/1981 | DeFonzo ................ 333/231 |
| 4,302,694 A | 11/1981 | Fujishima et al. | |
| 4,312,228 A | 1/1982 | Wohltjen | |
| 4,342,936 A | 8/1982 | Marcus et al. | |

(Continued)

FOREIGN PATENT DOCUMENTS

DE    4424422    1/1996

(Continued)

OTHER PUBLICATIONS

Fisch, M.R., et al., "Improved Acoustic Viscosimeter Technique", J. Acoust. Soc. Am., Sep. 1976, pp. 623-625, v. 60, No. 3.

(Continued)

*Primary Examiner*—Hezron Williams
*Assistant Examiner*—Rose M. Miller
(74) *Attorney, Agent, or Firm*—Senniger Powers (57) ABSTRACT

A sensor and methods for making and using the same in which a mechanical resonator is employed, comprising a resonator portion for resonating in a fluid without the substantial generation of acoustic waves; and an electrical connection between the resonator portion for oscillating and a source of an input signal; wherein the portion for resonating, the electrical connection or both includes a base material and a performance-tuning material that is different from the base material.

26 Claims, 7 Drawing Sheets

U.S. PATENT DOCUMENTS

| | | |
|---|---|---|
| 4,349,881 A | 9/1982 | November et al. |
| 4,361,026 A | 11/1982 | Muller et al. |
| 4,370,662 A | 1/1983 | Hou et al. |
| 4,391,338 A | 7/1983 | Patashnick et al. |
| 4,445,066 A | 4/1984 | Nishiyama et al. |
| 4,526,480 A | 7/1985 | Ward |
| 4,535,620 A | 8/1985 | Cunnungham |
| 4,543,829 A | 10/1985 | Lerch |
| 4,549,427 A | 10/1985 | Kolesar, Jr. |
| 4,596,697 A | 6/1986 | Ballato |
| 4,602,505 A | 7/1986 | Kanda et al. |
| 4,624,129 A | 11/1986 | Haynes |
| 4,644,803 A | 2/1987 | Ward |
| 4,696,181 A | 9/1987 | Rupprecht et al. |
| 4,721,874 A | 1/1988 | Emmert |
| 4,729,237 A | 3/1988 | Suzuki et al. |
| 4,734,609 A | 3/1988 | Jasime |
| 4,741,200 A | 5/1988 | Hammerle |
| 4,760,351 A | 7/1988 | Newell et al. |
| 4,767,719 A | 8/1988 | Finlan |
| 4,779,451 A | 10/1988 | Ezawa et al. |
| 4,782,332 A | 11/1988 | Cipris et al. |
| 4,783,987 A | 11/1988 | Hager et al. |
| 4,802,370 A | 2/1989 | EerNisse et al. |
| 4,802,384 A | 2/1989 | Schwarz et al. |
| 4,812,698 A | 3/1989 | Chida et al. |
| 4,862,384 A | 8/1989 | Bujard |
| 4,890,480 A | 1/1990 | Young |
| 4,893,496 A | 1/1990 | Bau et al. |
| 4,904,978 A | 2/1990 | Barth et al. |
| 4,910,523 A | 3/1990 | Huguenin et al. |
| 4,922,745 A | 5/1990 | Rudkin et al. |
| 4,970,492 A | 11/1990 | King |
| 5,006,845 A | 4/1991 | Calcar et al. |
| 5,179,028 A | 1/1993 | Valie et al. |
| 5,191,791 A | 3/1993 | Gerardi et al. |
| 5,201,215 A | 4/1993 | Granstaff et al. |
| 5,204,529 A | 4/1993 | Diatschenko |
| 5,224,174 A | 6/1993 | Schneider et al. |
| 5,235,844 A | 8/1993 | Bonne et al. |
| 5,253,530 A | 10/1993 | Letcher, III |
| 5,283,037 A | 2/1994 | Baer et al. |
| 5,296,374 A | 3/1994 | Culshaw et al. |
| 5,306,644 A | 4/1994 | Myerholtz et al. |
| 5,325,704 A | 7/1994 | Mariami et al. |
| 5,332,961 A | 7/1994 | Hammerle |
| 5,334,900 A | 8/1994 | Kawashima |
| 5,338,416 A | 8/1994 | Mlcak et al. |
| 5,357,964 A | 10/1994 | Spivey et al. |
| 5,361,632 A | 11/1994 | Magnani |
| 5,375,470 A | 12/1994 | Matsushima et al. |
| 5,421,190 A | 6/1995 | Brandle et al. |
| 5,434,650 A | 7/1995 | Nakahara et al. |
| 5,435,170 A | 7/1995 | Voelker et al. |
| 5,438,231 A * | 8/1995 | Khoshnevisan et al. .... 310/321 |
| 5,445,008 A | 8/1995 | Wachter et al. |
| 5,454,045 A | 9/1995 | Perkins et al. |
| 5,455,475 A | 10/1995 | Josse et al. |
| 5,464,509 A | 11/1995 | Mlcak et al. |
| 5,469,369 A | 11/1995 | Rose-Pehrsson et al. |
| 5,477,726 A | 12/1995 | Stabinger et al. |
| 5,488,866 A | 2/1996 | Ravel et al. |
| 5,524,477 A | 6/1996 | Wajid |
| 5,524,636 A | 6/1996 | Sarvazyan et al. |
| 5,528,924 A | 6/1996 | Wajid et al. |
| 5,531,091 A | 7/1996 | Gademann et al. |
| 5,533,402 A | 7/1996 | Sarvazyan et al. |
| 5,571,401 A | 11/1996 | Lewis et al. |
| 5,571,952 A | 11/1996 | Kauzlarich |
| 5,604,441 A | 2/1997 | Freese et al. |
| 5,622,223 A | 4/1997 | Vasquez |
| 5,653,939 A | 8/1997 | Hollis et al. |
| 5,661,233 A | 8/1997 | Spates et al. |
| 5,670,709 A | 9/1997 | Gallagher |
| 5,698,089 A | 12/1997 | Lewis et al. |
| 5,705,399 A | 1/1998 | Larue |
| 5,734,098 A | 3/1998 | Kraus et al. |
| 5,741,961 A | 4/1998 | Martin et al. |
| 5,741,962 A | 4/1998 | Birchak et al. |
| 5,744,902 A | 4/1998 | Vig |
| 5,770,038 A | 6/1998 | Iwama et al. |
| 5,776,359 A | 7/1998 | Schultz et al. |
| 5,777,210 A | 7/1998 | Voelker et al. |
| 5,789,665 A | 8/1998 | Voelker et al. |
| 5,792,938 A | 8/1998 | Gokhfeld |
| 5,798,452 A | 8/1998 | Martin et al. |
| 5,818,731 A | 10/1998 | Mittal et al. |
| 5,827,952 A | 10/1998 | Mansure et al. |
| 5,852,229 A | 12/1998 | Josse et al. |
| 5,885,849 A | 3/1999 | Di Stephano et al. |
| 5,889,351 A | 3/1999 | Okumura et al. |
| 5,915,499 A | 6/1999 | Few |
| 5,918,354 A * | 7/1999 | Ikegami et al. ............ 29/25.35 |
| 5,936,159 A * | 8/1999 | Kano et al. .............. 73/514.36 |
| 5,959,297 A | 9/1999 | Weinberg et al. |
| 5,985,356 A | 11/1999 | Schultz et al. |
| 6,023,961 A | 2/2000 | Discenzo et al. |
| 6,034,775 A | 3/2000 | McFarland et al. |
| 6,041,642 A | 3/2000 | Duncan |
| 6,044,694 A | 4/2000 | Anderson et al. |
| 6,126,311 A | 10/2000 | Schuh |
| 6,151,123 A | 11/2000 | Nielsen |
| 6,155,098 A | 12/2000 | Shapiro et al. |
| 6,157,449 A | 12/2000 | Hajduk |
| 6,175,409 B1 | 1/2001 | Nielsen et al. |
| 6,176,323 B1 | 1/2001 | Weirich et al. |
| 6,182,499 B1 | 2/2001 | McFarland et al. |
| 6,223,589 B1 | 5/2001 | Dickert et al. |
| 6,247,354 B1 | 6/2001 | Vig et al. |
| 6,260,407 B1 | 7/2001 | Petro et al. |
| 6,260,408 B1 | 7/2001 | Vig et al. |
| 6,265,226 B1 | 7/2001 | Petro et al. |
| 6,269,686 B1 | 8/2001 | Hahn et al. |
| 6,275,137 B1 | 8/2001 | Doppalapudi et al. |
| 6,286,363 B1 | 9/2001 | Discenzo |
| 6,294,388 B1 | 9/2001 | Petro et al. |
| 6,296,771 B1 | 10/2001 | Miroslav |
| 6,306,358 B1 | 10/2001 | Yamamoto |
| 6,311,549 B1 | 11/2001 | Thundat et al. |
| 6,327,890 B1 | 12/2001 | Galipeau et al. |
| 6,336,353 B2 | 1/2002 | Matsiev et al. |
| 6,371,640 B1 | 4/2002 | Hajduk |
| 6,393,895 B1 | 5/2002 | Matsiev et al. |
| 6,401,519 B1 | 6/2002 | McFarland et al. |
| 6,407,479 B1 | 6/2002 | Moellendorf et al. |
| 6,412,131 B1 | 7/2002 | Zhao et al. |
| 6,441,716 B1 | 8/2002 | Doppalapudi et al. |
| 6,456,096 B1 | 9/2002 | Ericson et al. |
| 6,459,995 B1 | 10/2002 | Collister |
| 6,494,079 B1 | 12/2002 | Matsiev et al. |
| 6,507,945 B1* | 1/2003 | Rust et al. .................. 717/103 |
| 6,509,749 B1 | 1/2003 | Buelna et al. |
| 6,511,915 B2 | 1/2003 | Mlcak |
| 6,519,034 B1 | 2/2003 | Engler et al. |
| 6,535,001 B1 | 3/2003 | Wang |
| 6,536,634 B2 | 3/2003 | Berndorfer et al. |
| 6,545,392 B2 | 4/2003 | Kawauchi et al. |
| 6,557,396 B2 | 5/2003 | Ismail et al. |
| 6,557,419 B1* | 5/2003 | Herb et al. ................... 73/766 |
| 6,564,126 B1 | 5/2003 | Lin et al. |
| 6,626,025 B2 | 9/2003 | Potyrailo et al. |
| 6,640,644 B1 | 11/2003 | Mireles et al. |
| 6,644,095 B2 | 11/2003 | Van Mullekom et al. |
| 6,658,429 B2* | 12/2003 | Dorsett, Jr. ................... 707/1 |

| | | | |
|---|---|---|---|
| 6,661,162 B1 | 12/2003 | Nagai et al. | |
| 6,664,067 B1 | 12/2003 | Hajduk et al. | |
| 6,928,877 B2 | 8/2005 | Carlson et al. | |
| 6,936,837 B2 * | 8/2005 | Yamada et al. | 257/2 |
| 2001/0010174 A1 | 8/2001 | Matsiev et al. | |
| 2002/0064649 A1 | 5/2002 | Lembke et al. | |
| 2002/0068488 A1 | 6/2002 | Tuller et al. | |
| 2002/0070841 A1 | 6/2002 | Doppalapudi et al. | |
| 2002/0074897 A1 | 6/2002 | Ma et al. | |
| 2002/0092340 A1 | 7/2002 | Prater et al. | |
| 2002/0113596 A1 | 8/2002 | Horie et al. | |
| 2002/0121132 A1 | 9/2002 | Breed et al. | |
| 2002/0137348 A1 | 9/2002 | Mlcak | |
| 2002/0148529 A1 | 10/2002 | Berndorfer et al. | |
| 2002/0162385 A1 | 11/2002 | Ismail et al. | |
| 2002/0162390 A1 | 11/2002 | Ismail et al. | |
| 2002/0178787 A1 | 12/2002 | Matsiev et al. | |
| 2002/0178805 A1 | 12/2002 | DiFoggio et al. | |
| 2002/0190814 A1 * | 12/2002 | Yamada et al. | 333/187 |
| 2002/0194906 A1 | 12/2002 | Goodwin et al. | |
| 2003/0000291 A1 | 1/2003 | Kolosov et al. | |
| 2003/0041653 A1 | 3/2003 | Matsiev et al. | |
| 2003/0041659 A1 | 3/2003 | Marszalek et al. | |
| 2003/0062910 A1 | 4/2003 | Wang et al. | |
| 2003/0083825 A1 | 5/2003 | Berndorfer | |
| 2003/0116497 A1 | 6/2003 | Carlson et al. | |
| 2003/0118078 A1 | 6/2003 | Carlson et al. | |
| 2003/0119060 A1 | 6/2003 | Desrosiers et al. | |
| 2003/0124028 A1 | 7/2003 | Carlson et al. | |
| 2003/0145647 A1 | 8/2003 | Ismail et al. | |
| 2003/0179002 A1 | 9/2003 | Beylich et al. | |
| 2003/0213292 A1 | 11/2003 | Budeiri et al. | |
| 2003/0222656 A1 | 12/2003 | Phillips et al. | |

FOREIGN PATENT DOCUMENTS

| | | |
|---|---|---|
| DE | 10014724 A1 | 9/2001 |
| EP | 0102490 B1 | 3/1984 |
| EP | 0 282 251 B1 | 3/1988 |
| EP | 0282251 | 9/1988 |
| EP | 0317356 B1 | 5/1989 |
| EP | 0676638 | 10/1995 |
| EP | 0 769 695 A | 4/1997 |
| EP | 0 779 510 | 6/1997 |
| EP | 0813236 | 12/1997 |
| GB | 1385488 | 8/1971 |
| GB | 2114745 | 8/1983 |
| GB | 2187286 | 9/1987 |
| JP | 57124236 | 8/1982 |
| JP | 59126931 | 7/1984 |
| JP | 60134617 | 7/1985 |
| JP | 05129874 | 5/1993 |
| JP | 08112613 A | 5/1996 |
| JP | 11094726 | 9/1997 |
| WO | WO 91/02975 | 3/1991 |
| WO | WO 95/13278 | 5/1995 |
| WO | WO 98/01739 | 6/1997 |
| WO | WO 98/15501 | 4/1998 |
| WO | WO 98/37412 | 8/1998 |
| WO | WO 99/18431 | 4/1999 |
| WO | WO 99/51980 | 10/1999 |
| WO | WO 00/58709 | 3/2000 |
| WO | WO 00/67086 | 11/2000 |
| WO | WO 01/77624 | 10/2001 |
| WO | WO 01/77624 A2 | 10/2001 |
| WO | WO 02/12265 | 2/2002 |
| WO | WO 02/16888 | 2/2002 |
| WO | WO 02/23134 | 3/2002 |
| WO | WO 02/077613 | 10/2002 |
| WO | WO 02/093136 A1 | 11/2002 |
| WO | WO 02/093740 A1 * | 11/2002 |
| WO | WO 03/014732 | 2/2003 |
| WO | WO 03/100390 | 4/2003 |
| WO | WO 03/054482 | 7/2003 |
| WO | WO 2004/036191 | 4/2004 |

OTHER PUBLICATIONS

Kanazawa, K. Keiji and Joseph G. Gordon II, "The Oscillation Frequency of a Quartz Resonator in Contact with a Liquid", Analytica Chimica Acta, 1985, pp. 99-105, Elsevier Science Publishers B. V., Amsterdam.

Kipling, Arlin L and Michael Thompson, "Network Analysis Method Applied to Liquid-Phase Acoustic Wave Sensors", Anal. Chem., 1990, pp. 1514-1519, 62.

Michels, A. et al., "1 MHz Quartz Length Extension Resonator as a Probe for Scanning Near-Field Acoustic Microscopy", Thin Solid Films, 1995, pp. 172-175, 264.

Muramatsu, Hiroshi et al., "Computation of Equivalent Circuit Parameters of Quartz Crystals in Contact with Liquids and Study of Liquid Properties", Anal. Chem., 1988, pp. 2142-2146, 60.

Muramatsu, H. et al., "A Quartz Crystal Viscosity Sensor for Monitoring Coagulation Reaction and Its Application to a Multichannel Coagulation Detector", Biosensors & Bioelectronics, 1991, pp. 353-358, 6, Elsevier Science Publishers Ltd. England.

Newsam, J. et al., "High Throughput Experimentation for the Synthesis of New Crystalline Microporous Solids," Microporous and Mesoporous Materials 48 (2001) 355-365.

Akporiaye, D. et al., "Combinatorial Chemistry—The Emperor's New Clothes?," Microporous and Mesoporous Materials 48 (2001) 367-373.

Hauptmann et al., Ultrasonic Sensors for Process Monitoring and Chemical Analysis; State-of-the-Art and Trends, 1998, pp. 32-48.

Jakoby et al., Viscosity Sensing Using a Love-wave Device, 1998, pp. 275-281.

Polla et al., Processing and Characterization of Piezoelectric Materials and Integration into Microelectromechanical Systems, 1998, pp. 563-597.

Pujari et al., Reliable Ceramics for Advanced Heat Engines, American Ceramic Society Bulletin, vol. 74, No. 4, Apr. 1995, pp. 86-90.

Manalis et al., Two-dimensional Micromechanical Bimorph Arrays for Detection of Thermal Radiation, Appl. Phys. Lett., vol. 70, No. 24, Jun. 16, 1997, pp. 3311-3313.

Lin et al., Operation of an Ultrasensitive 30-MHz Quartz Crystal Microbalance in Liquids, Analytical Chemistry, Vo. 65, No. 11, Jun. 1, 1993, pp. 1546-1551.

Li et al., Electromechanical Behavior of PZT-Brass Unimorphs, Journal of the American Ceramic Society, vol. 82, No. 7, 1999, pp. 1733-1740.

Cleland et al., Fabrication of High Frequency Nonometer Scale Mechanical Resonators from Bulk Si Crystals, Appl. Phys. Lett., vol. 69, No. 18, Oct. 28, 1996, pp. 2653-2655.

U.S. Appl. No. 09/420,334 entitled "Graphic Design of Combinatorial Material Libraries" (Lacy, et al.) filed on Oct. 18, 1999.

U.S. Appl. No. 09/550,549 entitled "Automated Process Control And Data Management System And Methods" (Crevier, et al.) filed on Apr. 14, 2000.

U.S. Appl. No. 09/285,963 entitled "Rapid Characterization of Polymers" (Safir et al.) filed on Apr. 2, 1999.

Matsiev, "Application of Flexural Mechanical Resonators to Simultaneous Measurements of Liquid Density and Viscosity", 1999 IEEE UltraSonics Symposium, pp. 457-460.

Nesbitt W. Hagood IV et al., "Development of Micro-Hydraulic Transducer Technology", 10th International Conference on Adaptive Structures and Technologies, Oct. 11-13, 1999, Paris, France.

Hoenk, Michael, et al.., "Surface Acoustic Wave Hygrometer: Measuring Water Vapor in Earth's Atmosphere," http://mishkin.jpl.nasa.gov, accessed Mar. 16, 2002, 7 pages.

Trolier, Susan et al., "Preparation of Chemically Etched Piezoelectric Resonators for Density Meters and Viscometers", Mat. Res. Bull., vol. 22, pp. 1287-1274 (1987).

H. Valimaki, J. Lekkala, H. Helle, "Evaluation of Equivalent Circuit Model for Thickness-Shear Mode Resonators in Liquids", Eurosensors X, Leuven, Belgium Nov. 9, 1996, S1377-1380.

H. Endo, K. Soda, I. Karube, H. Muramatsu, "Online Monitoring of the Viscosity in Dextran Fermentation Using Piezoelectric Quartz Crystal", Biotechnology and Bioengineering, vol. 36, S 636-641 (1990).

Mason, W. P., Hill M., "Measurment of the Viscosity and Shear Elasticity of Liquids by Means of a Torsionally Vibrating Crystal", Transactions of A.S.M.E., 69 (1947) 359-370.

Barnes C., "An in vitro urea sensor using a torsion-wave crystal device", Sensors and Actuators B, 8 (1992) 143-149.

Schmitt N. et al., "A new method based on acoustic impedance measurements for quartz immunosensors", Sensors and Actuators B43 (1997) 217-233.

Benes et al., "Viscosity Sensor Based on a Symmetric Dual Quartz Thickness Shear Resonator", pp. 1-7. 2003.

NSF Award Abstract #0239151, Feb. 6, 2003, pp. 1-2.

Nussbaum, "An Accurate Non-Radioactive Fluid Density Sensor", presentation to the Society of Petroleum Engineers, Bergen, Norway, Apr. 1, 2003.

Lec et al., "A Remote Acoustic Engine Oil Quality Sensor", 1997 IEEE UltraSonics Symposium, pp. 419-422.

Zhang et al, "Contributions of Amplitude Measurement in QCM Sensors", IEEE Transactions on Ultrasonics, Ferroelectrics, and Frequency Control, vol. 43, No. 5, Sep. 1996, pp. 942-947.

Smith et al., Water Sorption Isotherms and Enthalpies of Water Sorption by Lysozyme Using the Quartz Crystal Microbalance/heat Conduction Calorimeter, Biochimica et Biophysica Acta, Oct. 4, 2001, pp. 150-159.

Zhang et al.: "Determination of Liquid density with a low frequency mechanical sensor based on quartz tuning fork" Sensors and Auctuators B, Elsevier Sequoia S.A. Lausanne, CH. vol. 84, No. 2-3, May 15, 2002, pp. 123-128.

Shih et al.: Simultaneous Liquid Viscosity and Density Determination with Piezoelectric Unimorph Cantilevers: Journal of Applied Physics, American Institute of Physics. New York, U.S., vol. 89, No. 2, Jan. 15, 2001, pp. 1497-1505.

Dring et al.: "Integrated on-line multisensing of fluid flow using a mechanical resonator" Sensors and Actuators A, Elsevier Sequoia S.A., Lausanne, CH, vol. 85, No. 1-3, Aug. 25, 2000, pp. 275-279.

Greenwood et al., "Measurement of Viscosity and Shear Wave Velocity of a Liquid or Slurry for On-line Process Control", Ultrasonics 39 (2002) pp. 623-630.

Langdon, "Vibratory Process Control Transducers", The Marconi Review, Third Quarter, 1980, pp. 156-175.

A&D Weighing, SV Series User's Handbook V1.04E, p. 1-40, date unknown.

"@Kavlico . . . Our Sensors Are the Solution!", Kavlico, A Solectron Company, Capability Product Brochure—Industrial Sensors and Tranducers, date unknown.

"Automotive Engineering International Online: Top 50 Products for 1999", Product Info. List/Oil Quality Sensor, 1999, www.sae.org/automag/top50prod/17.htm, printed Feb. 5, 2004, p. 17.

Bohmer, Elemente der angewandten Elektrotechnik, p. 74-79, 1992, Translation attached.

"diScentris Cantilever Sensor Research Tool for Science and Industry", Veeco Instruments Inc. Brochure, 2003.

"CJV-5000 Vibro Viscometer Utilizing Tuning-Fork Technology", A&D Medical Weighing Test & Measurement Digital Testing and Measurement Products, Jan. 28, 2000, Yahoo Search printed Jun. 18, 2003.

"Field Trials of the Viscosity & Fluid Density Tool", Nan Gall Technology News Releases, Aug. 2002, www.nangall.com/products/plt/Fluid_Density_Tuned.htm, printed Feb. 14, 2003.

"EPSON presents in MC-30A: Reliable 32.768Hz Dedicated to Automotive Applications", Aug. 25, 2003, Electronic Devices Press Release, www.epson.com.sq.ntml.body_ed_press_25_aug_2003.html, printed Feb. 11, 2004.

Ferry, John D., "Viscoelastic Properties of Polymers", 1980, Chapters 5-8, p. 96-176, John Wiley & Sons, Inc.

Fleming, "The Vibrating Tuning Fork Fluid Density Tool", p. H1-H15, Nan Gall Technology Ltd, Aberdeen, Smith Institute, date unknown.

Fleming, "Theory of the vibrating tuning fork fluid density tool", Mar. 15, 2002, www.lancs.ac.uk.depts/physics/conf/esgi/NanGall/transducer.htm, printed May 7, 2003.

Fleming, "A Vibrating Tuning Fork Fluid Density Tool", Smith Institute Projects, last updated Jul. 15, 2002, www.smithinst.ac.uk/projects/NanGallESGI2002, printed Feb. 5, 2004.

Godemann, Ralph, "Refrigerant Flow in Evaporators", Heatcraft North America Transfer OEM Products Brochure, 2000, www.heatcraftoem.com/TechTopics/refrigerant_flow.htm.

Grate, et al. "Smart Sensor for Trace Organophosphorus and Organosulfur Vapor Detection Employing a Temperature-Controlled Array of Surface Acoustic Wave Sensors, Automated Sample Preconcentration, and Pattern Recognition", Analytical Chemistry, 1993, p. 1868-1881, vol. 65, No. 14.

Greenwood, Margaret, et al., "On line Sensor for Density and Viscosity Measurements of a Liquid or Slurry for Process Control in the Food Industry", Presented at Sensors and Control in Food Processing, Sixth Conference on Food Engineering, AIChE Annual Meeting, 1999, abstract.

Hammond, J.M. et al, "An Acoustic Automotive Engine Oil Quality Sensor*", Transducers '97, 1997 International Conference on Solid-State Sensors and Actuators, Chicago, Jun. 16-19, 1997, p. 1343-1346.

Hammond, J.M. et al, "An Acoustic Automotive Engine Oil Quality Sensor", IEEE International Frequency Control Symposium, 1997, p. 72-80.

Hlavay, J. et al., "Applications of the Piezoelectric Crystal Detector in Analytical Chemistry". Analytical Chemistry, 1977, p. 1890-1898, vol. 49, No. 13.

Karrai, "Lecture Notes on Shear and Friction Force Detection with Quartz Tuning Forks", Presented at the "Ecole Thematique du CNRS" on near-field optics, Mar. 2000, La Londe les Maures, France, p. 1-23.

Laine, E., et al., "Device for the Investigation of the Humidity-Related Behaviours of Materials", 1986, Department of Physics, University of Turku, Finland.

Landau, L.D., et al., "Fluid Mechanics", "Viscous Fluids; Oscillatory Motion in a Viscous Fluid", 1959, p. 96-97, Pergamon Press Ltd.

"The Lubri-Sensor Electronic Oil Quality Analyser", www.pmlubricants.com.au/pm_lube_concept/lubri-sensor.htm, Eco Oil Pty. Ltd., Copyright 1997-2004, printed Feb. 5, 2004, p. 1-2.

Matsiev, L.F., "Application of Flexural Mechanical Resonators to High Throughput Liquid Characterization" 2000 IEEE International Ultrasonic Symposium, San Juan, Puerto Rico (Oct. 22-25, 2000), p. 427-434.

Merhaut, Josef, "Theory of Electroacoustics", "Theory of Mechanical Systems with Distributed Elements", 1981, p. 100-101, McGraww-Hill International Book Company.

Muramatsu, et al., "Viscosity Monitoring with a Piezoelectric Quartz Crystal and its Application to Determination of Endotoxin by Gelatin of Limulus Amebocyte Lysate", Analytica Chimica Acta, 1988, p. 91-98, 215, 1988 Elsevier Science Publishers B.V.

Nomura, et al., "Electrolytic Determination of Nanomolar Concentrations of Silver in Solution with a Piezoelectric Quartz Crystal", Analytica Chimica Acta, 1981, p. 97-102, 131, Elsevier Scientific Publishing Company.

Oden, P.I., et al., "Viscous drag measurements utilizing microfabricated cantilevers", Applied Physics Letters, Jun. 24, 1996, p. 3814-3816, 68(26).

Puuman, "Hygroscopicity Measurement Apparatus", date unknown, http://web.archive.org/web/20010405220058/www.puuman.com/hma.htm.

"Sensors", Actuators Components Sensors Applications Process Technology System Integration Deutsch, Fraunhofer Verbund Mikroelektronik, 2001, www.izm.fhg.delvue/seiteniseiten_neulenglish/sensoren_e.html, printed Oct. 3, 2002.

"Sensors at Actuators Intellek Oil Condition Sensor", Delphi Corporation, www.delphi.com, date unknown.

"The Future of Pressure and Temperature Measurement—A Lifetime of Accuracy" Senstronics Storm Brochure, date unknown.

"SINIMS Oil and Gas Workshop", ICMS, Edinburgh, Mar. 11, 2002.

"SOS Smart Oil Sensor", Impact Technologies LLC Brochure, 2003.

Surface Acoustic Wave (SAW) Hygrometer (Micro Weather Station), last updated Feb. 14, 2001, http://technology.ipl.nasa.gov/gallery/gl_pages/saw.html.

Wright, Dr. Robert, et al., "Sensor Technology Improves Jet Engine Reliability", printed Feb. 5, 2004, www.afrlhorizons.com/Briefs/June01/PR0003.html, p. 1-2.

Wullner, D., et al. "Multi-Function Microsensor for Oil Condition Monitoring Systems", AMAA Paper 030305b, 2003, p. 1-5.

"ViscoMaster HFO Viscosity Transmitter for Marine and Power Applications", Solartron Mobrey Brochure, Jan. 2002.

Zeisel et al, "A Precise and Robust Quartz Sensor Based on Tuning Fork Technology for ($SF_6$)-gas density control", Sensors and Actuators (2000) p. 233-236, vol. 80.

Viscosity and Density Sensing with Ultrasonic Plate Waves, B.A. Martin, S.W. Wenzel, and R.M. White, Sensors and Actuaturs, A21-A23 (1990), 704-708.

"Micromachined viscosity sensor for real-time polymerization monitoring", O.Brand, J.M. English, S.A. Bidstrup, M.G. Allen, Transducers '97, 121-124 (1997).

"Frequency response of cantilever beams immersed in viscous fluids with applications to the atomic force microscope", J.E. Sader, J. Appl. Phys. 84, 64-76 (1998).

"Resonance response of scanning force microscopy cantilever", G.Y. Chen, R.J. Warmack, T.Thundat, and D.P. Allison, Rev. Sci. Instrum. 65, 2532-2537(1994).

"Lecture notes on shear and friction force detection with quartz tuning forks" Work presented at the "Ecole Thematique du CNRS" on near-field optics, Mar. 2000, La Londe les Msures, France by Khaled Karrai, Center for.

J. Sorab, G.S. Saloka: "Engine Oil Viscosity Swnsors Using Disks of PZT Ceramic as Electromechanical Vibrators" Society of Automotive Engineers SAE, No. 971702, 1997.

* cited by examiner

FIG. 12

MECHANICAL RESONATOR

CLAIM OF PRIORITY

This application claims the benefit of U.S. Provisional Application No. 60/456,767 filed on Mar. 21, 2003.

TECHNICAL FIELD

The present invention is directed to improvements in the fabrication and use of mechanical resonators for measuring various properties of fluids (including both liquids and vapors).

BACKGROUND ART

The use of mechanical resonators for measuring properties of materials, including liquid and vapor phases, has been disclosed in commonly-owned U.S. Pat. No. 6,336,353 (Matsiev, et al.)("Method and apparatus for characterizing materials by using a mechanical resonator"); and U.S. Pat. No. 6,182,499 (McFarland, et al.) ("Systems and methods for characterization of materials and combinatorial libraries with mechanical oscillators"); and U.S. patent application Ser. Nos. 09/723,818, 09/800,819, and 09/133,171; published U.S. Patent Application No. 20030000291; and U.S. patent application Ser. No. 10/155,207 ("High Throughput Microbalance and Methods of Using Same") (filed May 24, 2002), all of which are hereby expressly incorporated by reference for all purposes.

It has been observed that a preferred resonator is one that is operated at a relatively low frequency, e.g. below about 1 MHz; however, resonators may be operated at higher frequencies. For example, a highly preferred resonator is one that employs at least one cantilever end, and more preferably a plurality of cantilever ends, such as would be found in a tuning fork.

The above patent documents disclose the employment of various alternative resonators, such as tridents, cantilevers, torsion bars, bimorphs, or membrane resonators.

The documents also address the possibility of coating resonators with a coating for sensitivity to certain chemicals, wear resistance, for environmental protection or for some other functionality.

As the success of resonators for use in sensing applications has grown, the environments within which the resonators are expected to perform have likewise increased. In particular, the desire for increasing resonator life in high stress, abrasive and/or chemically aggressive environments has driven the search for improved specific material and structural combinations.

SUMMARY OF THE INVENTION

The present invention is directed to improvements in sensing devices and systems employing mechanical resonators, and particularly improvements to structure and material combinations suitable especially for extreme operating conditions, such as encountered without limitation in harsh environments (e.g., oil fields, operating machinery fluids, chemical processing or otherwise), or where micro-scale or even nano-scale sensitivity is crucial to successful performance (e.g., for measuring hygroscopicity, for flow injection analysis, for high throughput parallel or rapid-serial screening or otherwise).

Accordingly, one aspect of the present invention is directed to the employment of a combination of materials in a mechanical resonator (and most preferably a tuning fork resonator) in which materials alternative or in addition to quartz crystals are employed.

In another aspect of the present invention, a highly preferred configuration for a tuning fork for use in a sensor is employed, pursuant to which the shape of the tuning fork is generally that of an "H" or a modified "H".

In one preferred embodiment, the resonators according to the present invention are placed in a fluid and a signal is applied to the resonator. A characteristic of the fluid is determined based upon the resonator response. In one even more highly preferred embodiment, the resonators according to the present invention are placed in a fluid and a variable frequency input signal is applied to the resonator. The frequency of the signal is varied and the frequency and a characteristic of the fluid is determined based upon the resonator response.

DETAILED DESCRIPTION OF THE PREFERRED EMBODIMENTS

The present invention is directed primarily to a method using a mechanical piezoelectric resonator ("mechanical resonator") for measuring physical and electrical properties, such as the viscosity, the density, the viscosity density product, the impedance, the dielectric capacitance, the dielectric constant, and the conductivity of sample liquid compositions. The detailed description below focuses primarily on mechanical resonators, and specifically tuning fork resonators. However, the principles of the invention can also be applied to thickness shear mode ("TSM") resonators, such as a resonator having a quartz crystal sandwiched in between electrodes. Thus the present invention has applicability to resonators that are oscillated such that a portion of the structure of the resonator is passed through a fluid such as tridents, cantilevers, torsion bars, unimorphs, bimorphs, membrane resonators or combinations thereof.

The employment of any of a variety of different art-disclosed measurement systems may be made in accordance with the present invention, and the discussion of a preferred variable frequency input signal system is not intended as limiting.

Nonetheless, pursuant to a preferred variable frequency input signal system, a mechanical resonator according to the present invention is connected to a measuring system that sends a variable frequency input signal, such as a sinusoidal wave, that sweeps over a predetermined frequency range, preferably less than about 100 kHz (e.g., in the 25–30 kHz range) for a tuning fork resonator and in a higher range for the TSM resonator. The resonator response over the frequency range is then monitored to determine selected physical and electrical properties of the fluid. Absolute values may be obtained if desired, as may relative, comparative or index values. Additionally, it is possible also that the system of the present invention may be employed with determining whether a certain threshold criteria is met in the fluid being analyzed.

The hardware for the present measuring system may be any suitable hardware. It may include, for example, art-disclosed network analyzers, see, e.g., U.S. Pat. No. 6,336,353 (Matsiev, et al.)("Method and apparatus for characterizing materials by using a mechanical resonator"); and U.S. Pat. No. 6,182,499 (McFarland, et al.) and published U.S. Patent Application No. 20030000291, hereby incorporated by reference. The hardware might also be part of an application specific integrated circuit (ASIC), such as is disclosed for example in commonly owned, co-pending application entitled "Integrated measurement assembly for a machine fluid sensing system" (U.S. patent application Ser. No. 10/452,264), hereby incorporated by reference, as disclosed in commonly owned, co-pending application entitled "Application specific integrated circuitry for controlling analysis of a fluid" (PCT/US04/08555), claiming benefit of U.S. provisional application No. 60/419,404), hereby incorporated by reference, as disclosed in co-owned, co-pending application entitled "Resonator Sensor Assembly" (10/804,379, PCT/US05/08531 and PCT/US04/08522, claiming benefit of U.S. provisional 60/456,517), as disclosed in co-owned, co-pending application entitled "Environmental Control System Fluid Sensing System And Method" (International patent application no. US03/32983) or as disclosed in co-owned, co-pending application entitled "Mechanical Resonators" (PCT/US04/08526, claiming benefit of U.S. provisional application No. 60/452,292). All of the foregoing are hereby incorporated by reference.

Generally, the hardware for measuring system provides a versatile fluid sensing system. More specifically, the hardware provides a fluid sensing system for machines that rely upon the presence, condition or both of a fluid to maintain efficient operation, such as (without limitation) a synthetic or natural engine oil. In an automotive application, the user is provided with the ability to determine the actual condition (e.g. or the relative deviation of the state of the engine oil from its initial or virgin state) of the engine oil at any particular time, including during operation. Alternatively, in conjunction with assessing fluid condition, the hardware may also determine the amount of fluid remaining in a reserve of an assembly. This advantageously allows machine operators to extend the duration between fluid service events, while helping to assure continued operational integrity of a machine.

Any dynamic assembly that depends on fluids to operate (e.g., where friction and heat are of a concern), will benefit from hardware capable sensing the state of a fluid. For instance, the ability to dynamically monitor fluid condition, process data obtained from the monitoring, and report characteristics of the fluid to an interface or operator can have many applications. Assemblies that may benefit from the defined embodiments of the present invention are many, and can include without limitation, engines in general, automobiles, heavy machinery, military equipment, airplane parts, oil drilling, exploration and production well logging, oil refining, pipeline and quality control applications, marine transportation, sub-sea exploration and aerospace related equipment, or any other fluid containing application. In addition, contemplated methods include a step of assembling the hardware into a device that is incorporated into engines in general, automobiles, heavy machinery, military equipment, airplanes, oil drilling, exploration and production well logging equipment, oil refining, pipeline and quality control equipment, marine transportation equipment, sub-sea exploration and aerospace related equipment, or any other equipment that utilizes fluids for operations.

In the automotive field, numerous components require lubrication, which is not limited to engine oil. For example, other automotive components may include the transmission, the transfer case, the differential, etc. Still further, the sensing system may further be used to determined the quality and amount of other fluids which are not necessarily used predominantly as a lubricant, including: brake fluids, steering fluids, antifreeze fluids, refrigerant fluids, windshield washer fluids, or any other fluid located in an automotive system.

In one embodiment of suitable hardware, an oil sensing system is used to determine the component characteristics and amount of engine oil. In an automotive application, the oil sensing system will provide a user, at a minimum, with a warning as to the need to change the oil (such as owing to the presence of contaminants, a breakdown or loss of useful ingredients or otherwise). In such an application, the warning is essentially informing the user of the automobile that the engine oil has reaches a quality level or condition that is lower than that recommend by the automobile's manufacturer (or set by the oil manufacturer).

The fluid sensing system preferably uses a mechanical resonator as the fluid sensor in accordance with the present invention. The mechanical resonator is at least partially contained in the fluid under-test. To monitor the condition of the fluid under-test (i.e., engine oil), the mechanical resonator is provided with electrical energy through a frequency generator. The frequency generator is designed to apply a frequency signal (to the mechanical resonator) that is swept over a predetermined frequency range. Electronics are then used to detect the response signal from the mechanical resonator and process the signal to ascertain characteristics of the fluid under-test. In an embodiment of the fluid sensing system, the electronics are provided in the form of an application specific integrated circuit (ASIC). In addition, the hardware might also be part of or include a field programmable gate array (FPGA).

The present invention may suitably be employed in a package that is at least partially encapsulated, so as to expose the resonator to the fluid being tested, but otherwise protect fragile components, such as is disclosed for example in commonly owned, co-pending application entitled "Resonator sensor assembly and method" (60/456,517).

The packaging for the present sensor provides a protective mounting structure for the sensor and other associated components during installation and use; the sensor may advantageously be incorporated on to a platform to form a sensor package. Such a configuration would allow the sensor to be in contact with a fluid while protecting associated components from the harsh environment typically found in dynamic systems and any abuse associated with the installation of the same. In a preferred arrangement, the sensor package would comprise a sensor element, having an exposed sensing surface, attached to a substrate such that the exposed sensing surface is spaced from the platform. Advantageously, the sensor package may be further configured with other components to facilitate the determination of the quality of a fluid. Such components may comprise, a housing, a resistance temperature sensor, an application specific integrated circuit (ASIC), and/or a conduit for communicating with other components. As such, it may be desirable to coat all or some of the additional components and a portion of the sensor with a protective coating.

In the foregoing description, numerous specific details are set forth in order to provide a thorough understanding of the fluid sensing system, hardware and packaging that may be used with the present invention. It will be apparent, however, to one skilled in the art that the present invention may be practiced without some or all of these specific details. In other instances, well known process steps have not been described in detail in order not to unnecessarily obscure the present invention.

In accordance with a preferred embodiment of the present invention, there is disclosed an improved material system for use as a resonator. The material system is predicated upon the substitution of all or part of a piezoelectric material (e.g. quartz crystal) with a performance-tuning material that improves the characteristics of the resonator for use in a medium that has high temperature, is corrosive, is subject to abrasives, or a combination thereof, when compared with the characteristics of a resonator that consists essentially of quartz crystal.

Figure 1:
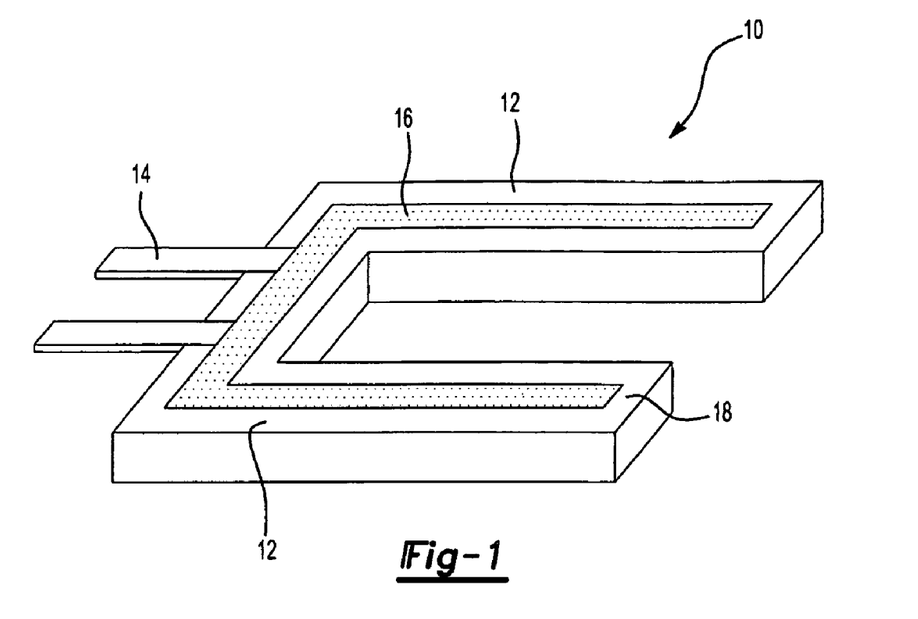
FIG. 1 is a perspective view of one illustrative resonator in accordance with the present invention.

FIG. 1 shows a perspective view of one preferred resonator 10 of the present invention. The resonator 10 preferably has one or more tines 12 including a piezoelectric material and at least one electrode 14 (or suitable structure for receiving the electrode) connected to the piezoelectric material. A performance-tuning material 16 is included on a base material 18.

Figure 3:
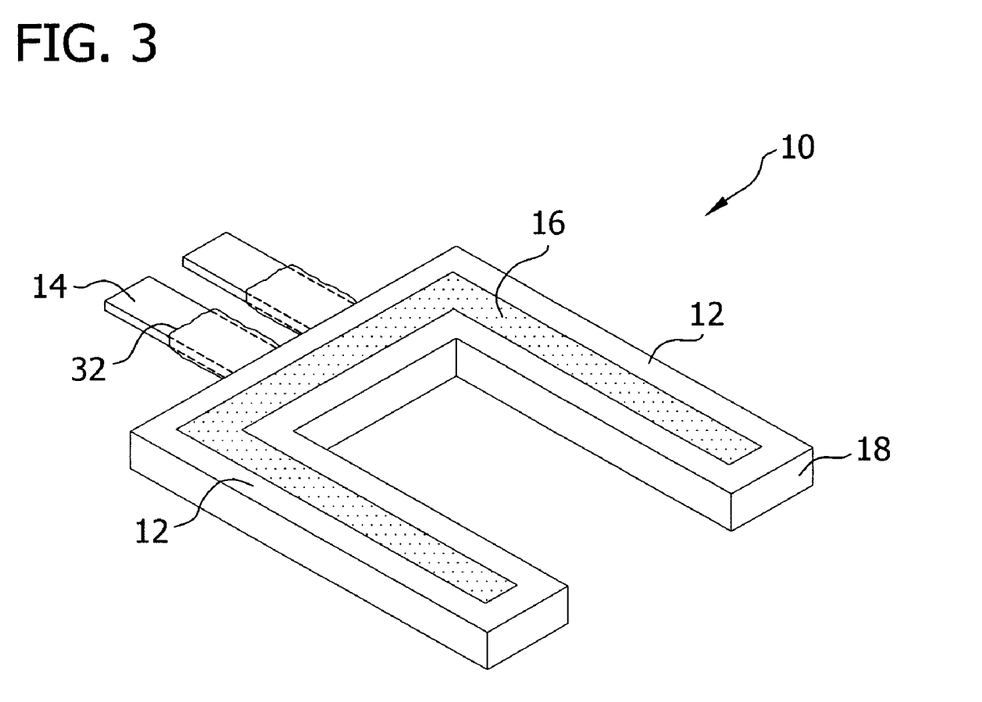
FIG. 3 is a perspective view of another resonator showing a dielectric material partially covering electrodes of the resonator.

The use of a metal is most preferred for the electrodes. However, other conductive materials may also be employed, such as conductive polymers, carbon or otherwise. Preferred metals are pure metals or alloys including a metal selected from gold, platinum, silver, chromium, aluminum, nickel, titanium or mixtures thereof. Other noble or transition metals may also be employed. The electrodes 14 may be covered, in whole or in part, by a dielectric material 32 (e.g., as shown in FIG. 3).

The base materials of the resonators of the present invention preferably are selected from at least one type of device of piezoelectric materials, electrostrictive materials, magetostrictive materials, piezoresistive materials, elasto-optic materials, anisotropic materials, or combinations thereof. By way of example, the particular material may be a metallic material, a crystalline material, a ceramic material or a combination thereof. Examples of suitable materials include, without limitation, quartz, lithium niobate, zinc oxide, lead zirconate titanate (PZT), gallo-germanates (e.g., Langasite ($La_3Ga_5SiO_{14}$), Langanite, or Langatate), diomignite (lithium tetraborate), bismuth germanium oxide, gallium phosphate, gallium nitride, aluminum nitride or combinations thereof. The preferred base materials may be undoped or doped with art-disclosed dopants.

Any suitable technique may be used to manufacture the resonator. For example, in one aspect, the resonators are prepared by art-disclosed processing techniques, such as are practiced in the semiconductor device fabrication industry. Thus, a wafer may be provided, one or more layers deposited thereon (e.g., by vapor deposition, sputtering, spin coating, curtain coating, laminating wafer bonding, or the like). Steps may be performed for shaping the resonator, such as photolithography, laser cutting, etching, dicing or the like. Other fabrication techniques, such as casting, molding, or the like may also be used.

Figure 2:
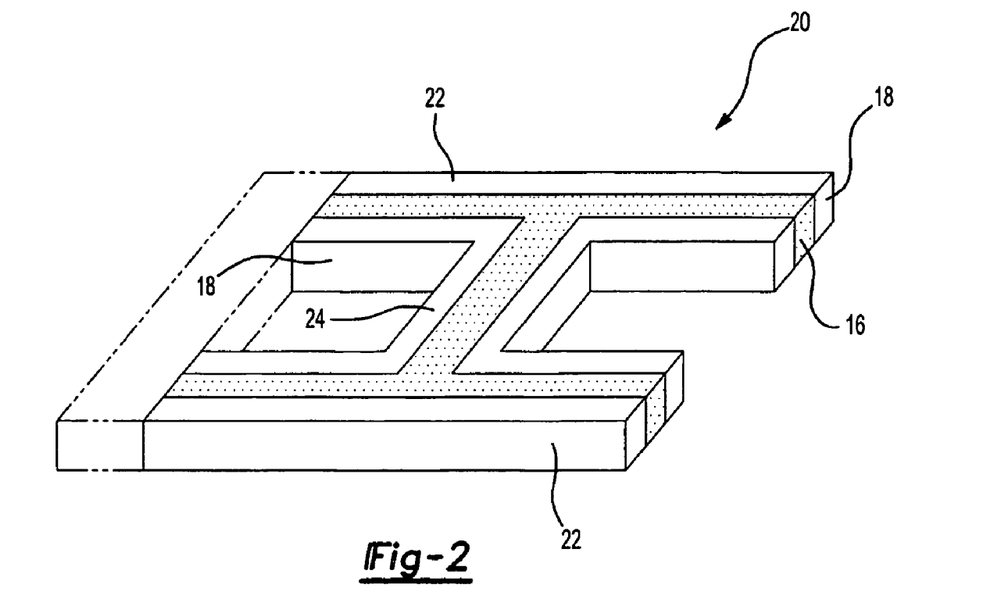
FIG. 2 is a perspective view of one illustrative resonator in accordance with the present invention.

FIG. 2 illustrates an alternative structure for a resonator 20, in which the resonator has tines 22 that join at a cross member 24 to define a generally "H" shaped configuration. The structure of FIG. 2 can also include a performance-tuning material 16 on or within at least one of its surfaces as taught herein. In yet another aspect of the invention the "H" shaped configuration is modified to include at least two cross members, one of which might be located at the ends of opposing tines as shown in phantom in FIG. 2.

The resonator configurations shown in FIGS. 1 and 2 are not intended as limiting. The resonators may have tines that are of constant cross sectional area along their length, varying cross sectional area along their length, or combinations thereof. The tines can be tapered as desired. They may have sharp edges, rounded edges or combinations thereof.

Preferably the dimensions of the resonators for use in accordance with the present invention are such that the total volume of the resonator including the performance-tuning material is less than about 75 $mm^3$, more preferably less than about 50 $mm^3$, still more preferably less than about 25 $mm^3$, and even still more preferably less than about 15 $mm^3$. One highly preferred resonator has tines that do not exceed about 15 mm in its longest dimension, and more preferably is smaller than about 8 mm in its longest dimension. A preferred resonator has a thickness no greater than about 2 mm, and more preferably no greater than about 1 mm. By way of example, without limitation, one illustrative resonator is about 0.5×3×5 mm in dimension. Of course, larger resonators may also be employed and the present invention is not limited only to small resonators. For example, the use of the present invention by employment of a resonator that is about 1 to about 250 cm, and more preferably about 50 to about 100 cm in length is possible. Larger resonators may be suitable for use in multiphase fluids (e.g. emulsions) and may be more robust and easier to manufacture.

It will be appreciated that even though only certain examples are provided, the method and system of the present invention can use other types of resonator, without departing from the spirit and scope of the invention.

One characteristic that is desirable and may be found in the resonator materials or performance tuning materials of the present invention is a relatively high degree of hydrophobicity or hydrophilicity.

Among the preferred characteristics of the resonators of the present invention is the base material is generally thermally stable. For example, in one preferred embodiment, the material exhibits a dielectric constant that is substantially constant over a temperature range of about 0° C. to about 100° C., more preferably about −20° C. to about 150° C., and still more preferably about −40° C. to about 200° C. For example, it is contemplated that a preferred material exhibits stability to a temperature of at least about 300° C., and more preferably at least about 450° C. In another aspect, the dielectric constant of the performance-tuning material preferably is greater than that of quartz alone, such as by a factor of 5 or more, more preferably by a factor of 10 or more and still more preferably by a factor of 20 or more.

A highly preferred base material will not undergo a phase transformation up to a temperature of at least 500° C., and more preferably at least 1000° C.

A preferred characteristic of the performance tuning material is that it is relatively hydrophobic and exhibits a relatively low porosity, e.g., less than about 5% of its volume, more preferably less than about 3% and still more preferably less than about 1% and even still more preferably less than about 0.1%. A preferred performance tuning material will be stable at about 150° C. Preferably it will be resistant to absorption of oils.

Examples of particularly preferred performance-tuning materials include one or a combination of two or more materials selected from the group consisting of polymers, ceramics, diamond, diamond-like carbon (e.g., Diamonex® DLC), and combinations thereof. For example, preferred performance-tuning materials might include one or a combination of two or more materials selected from the group consisting of fluoropolymers, silicones, silanes, polyolefins, carbides, nitrides, oxides, diamond, diamond-like carbon, and combinations thereof; and even more particularly might include one or a combination of two or more materials selected from the group consisting of polytetrafluoroethylene, fluorosilicone, polyethylene (e.g., high density polyethylene), polypropylene (e.g., high density polypropylene), silicon carbide, silicon nitride, diamond, diamond-like carbon, and combinations thereof. One preferred performance-tuning material includes polymers of the para-xylylenes (generically called parylenes), and more preferably polymers of para-xylyenes with one or more fluorine atoms in the ring (generically called parylene HT). It is also possible that a material selected from the above identified examples of base materials may be employed as a performance tuning material.

Figure 4:
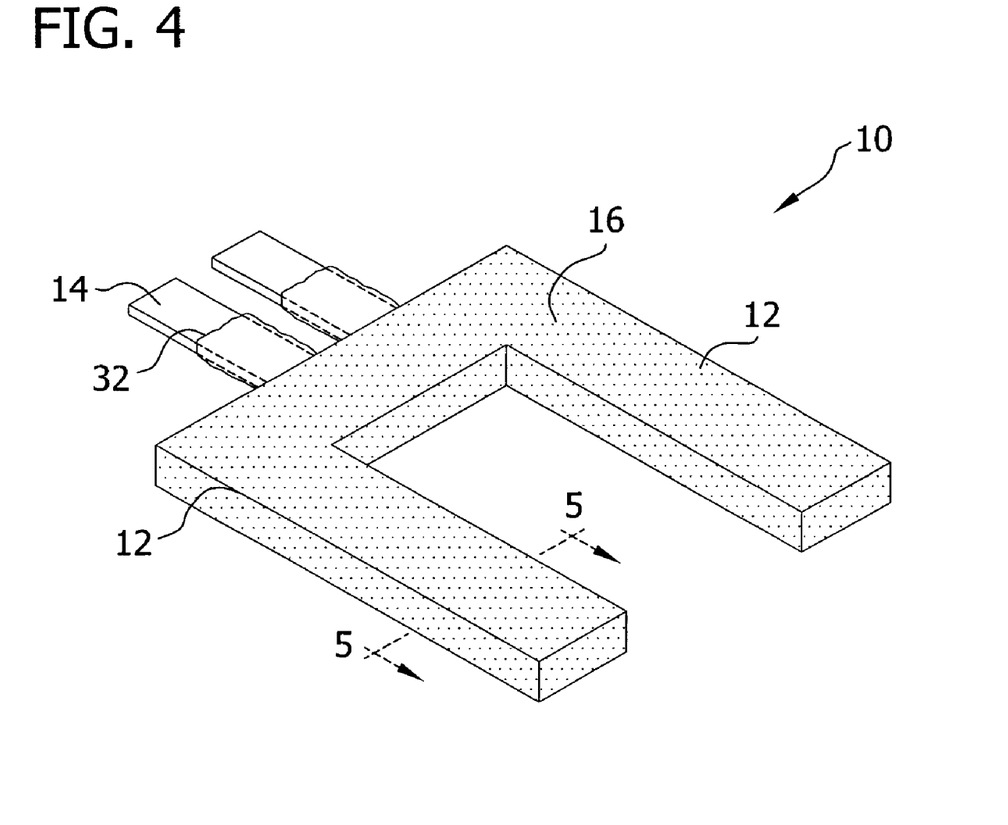
FIG. 4 is a perspective view of a resonator having a performance tuning material dispersed within a base material.
Figure 5:
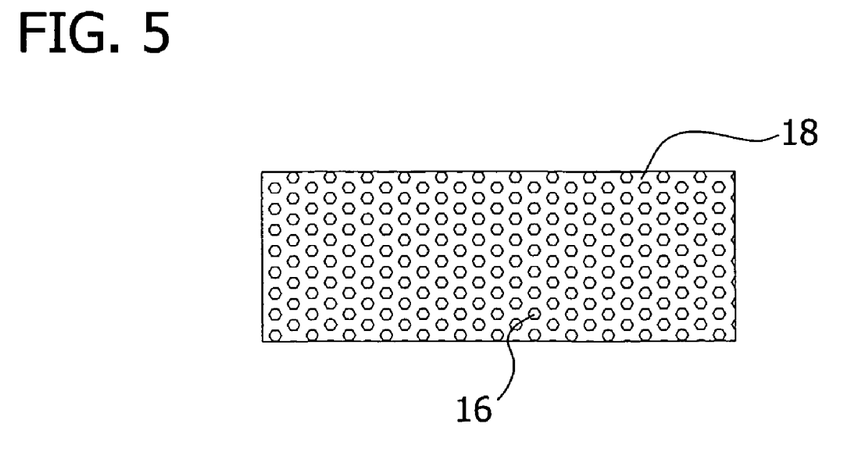
FIG. 5 is a cross section through a tine of the resonator shown in FIG. 4.
Figure 6:
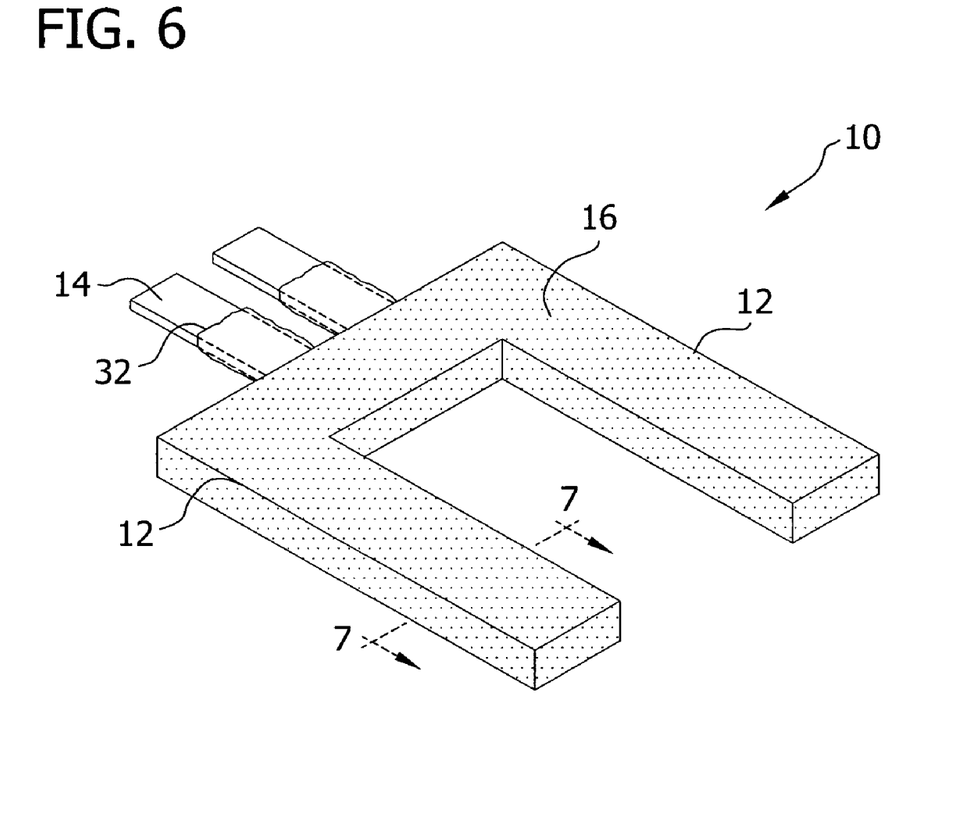
FIG. 6 is a perspective view of a resonator having a performance tuning material including a layer entirely overlying a base material.
Figure 7:
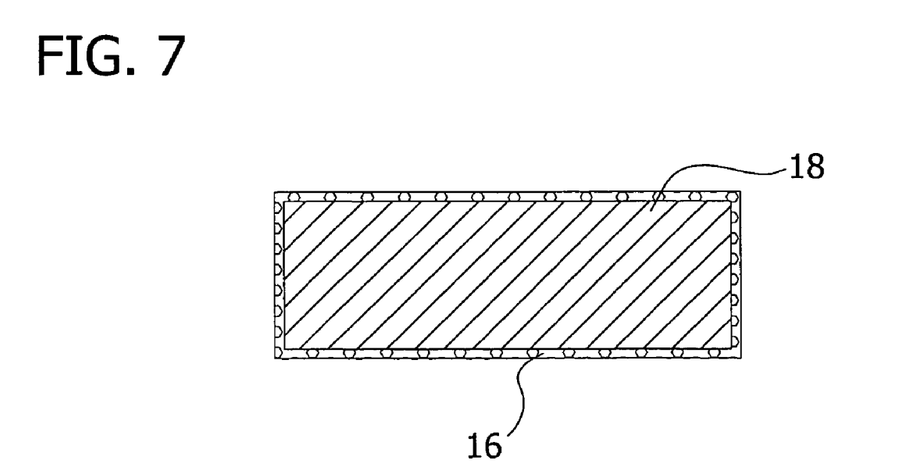
FIG. 7 is a cross section through a tine of the resonator shown in FIG. 6.
Figure 8:
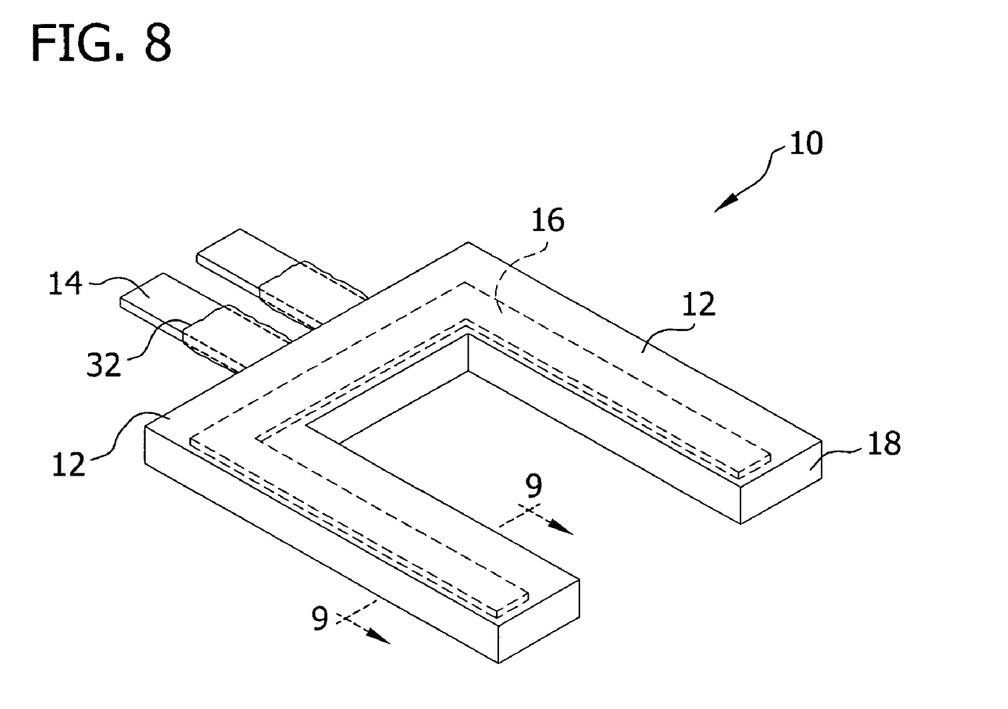
FIG. 8 is a perspective view of a resonator having a performance tuning layer that is an intermediate layer in the base material.
Figure 9:
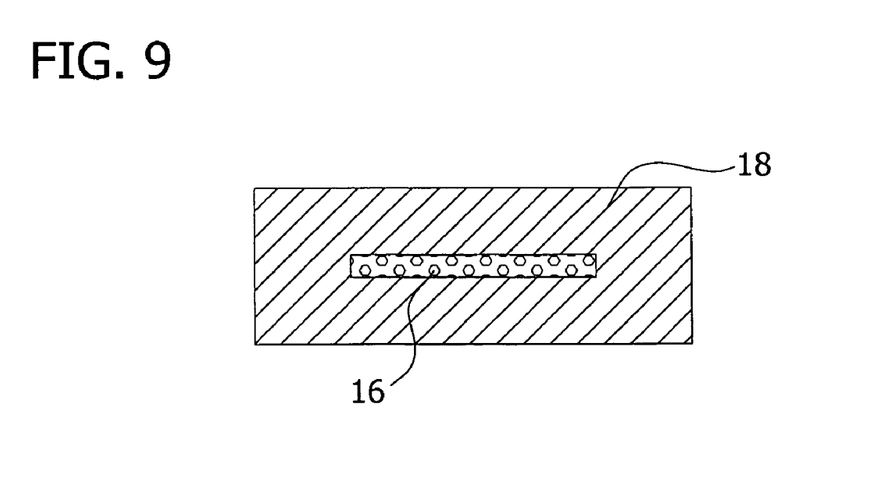
FIG. 9 is a cross section through a tine of the resonator shown in FIG. 8.
Figure 10:
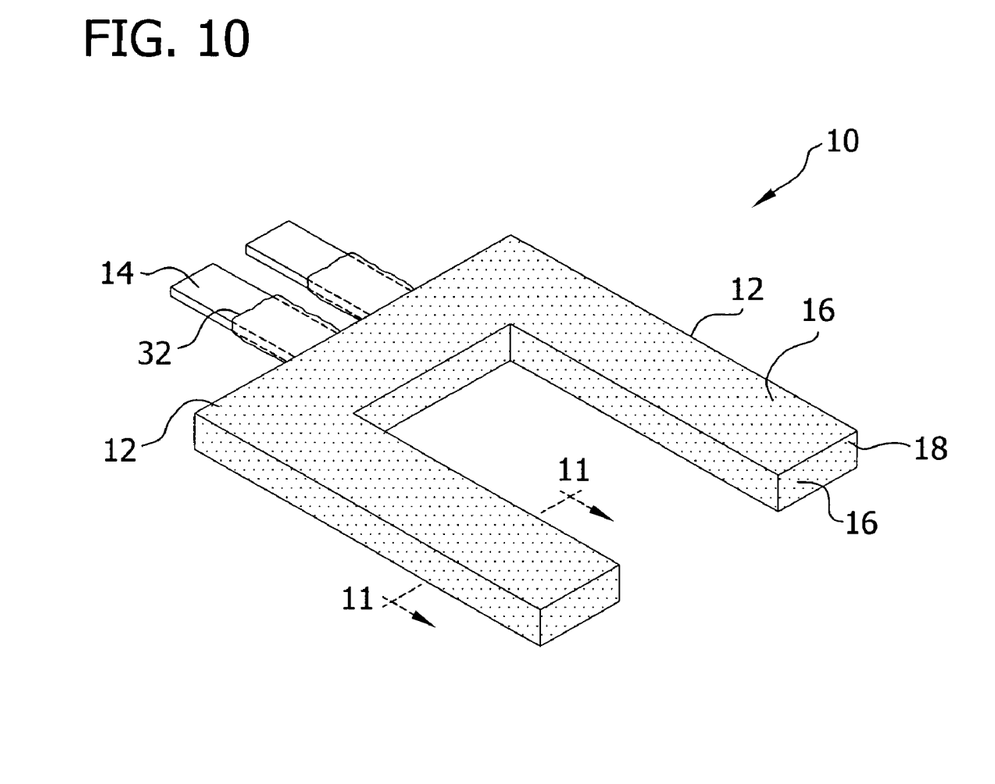
FIG. 10 is a perspective view of a resonator having a performance tuning material including a layer entirely overlaying a base material and a layer that is an intermediate layer in the base material in combination.
Figure 11:
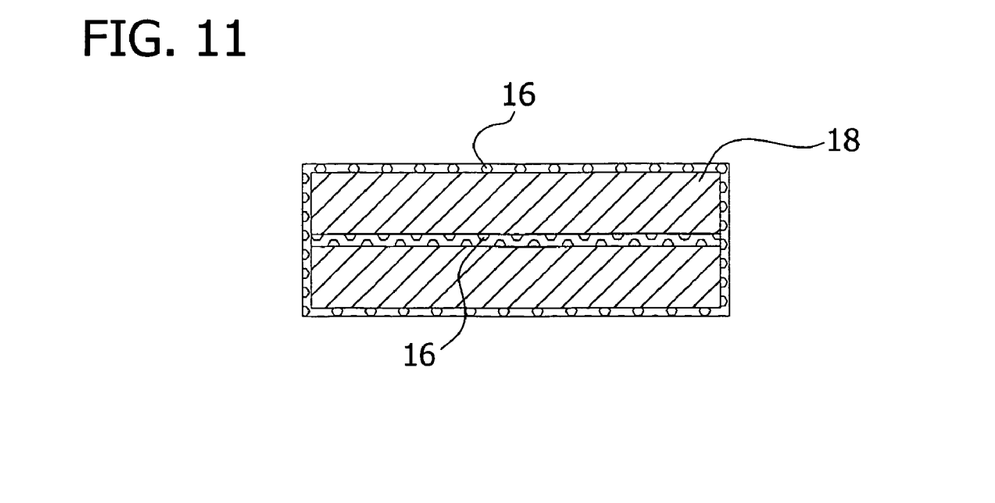
FIG. 11 is a cross section through a tine of the resonator shown in FIG. 10.
Figure 12:
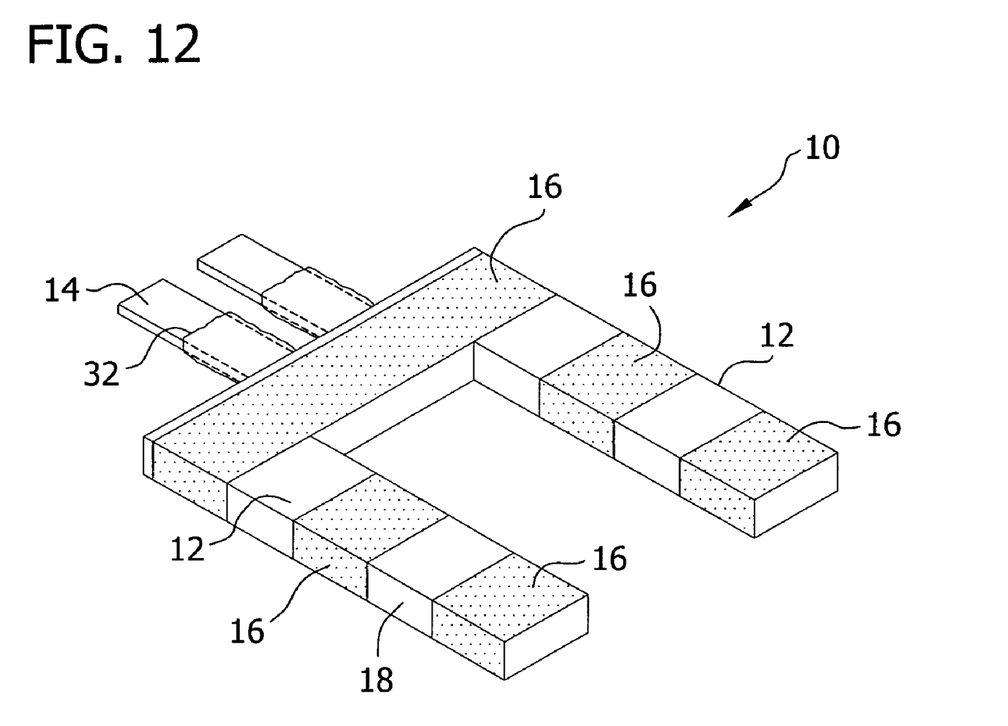
FIG. 12 is a perspective view of a resonator having performance tuning material that is an intermittent layer along edges of the base material.

The performance tuning materials of the present invention can be incorporated into a resonator in any of a number of different forms. By way of example, the performance tuning materials 16 might be applied as one or a plurality of layers partially overlying a base resonator material 18 (e.g., quartz crystal), as shown in FIG. 1, for example; as one or a plurality of layers entirely overlying a base resonator material (e.g., as shown in FIGS. 6 and 7); as the entirety of the resonator material; as an intermediate layer in the resonator (e.g., as shown in FIGS. 8 and 9); as a matrix material having a different material dispersed therein (e.g., as shown in FIGS. 4 and 5); as a material dispersed within a different matrix material; or combinations thereof (e.g., as shown in FIGS. 10–11). When employed as a layer, the performance tuning material may be employed continuously (e.g., as shown in FIG. 6) or intermittently (e.g., as shown in FIG. 12), along edges of the resonator base material (e.g., as shown in FIGS. 6 and 12), within the interior of the resonator base material (e.g., as shown in FIGS. 8 and 9), or a combination thereof (e.g., as shown in FIGS. 10 and 11). One or more of the performance tuning materials may also be employed to coat electrodes of sensors in accordance with the present invention.

One or a plurality of layers of the performance tuning materials therefore may be fabricated into a resonator using any of a number of different art-disclosed techniques, such as one or a combination of solvent coating, laser ablation, plasma deposition, physical vapor deposition, chemical vapor deposition, in situ polymerization, dipping, adhesive bonding, sintering, plating, fastening, chemical bonding or a combination thereof. By way of example, in one embodiment, a surface coating is applied to a resonator by masking the resonator and depositing performance-tuning material over the unmasked region. A step of photolithography may also be employed using suitable photoresist in order to achieve even more precise control over the size and shape of the coating. Preferably the deposition processing temperature is maintained below about 500° C., and more preferably below about 250° C.

Any coating process may also be accompanied with a suitable cleaning step, such as a rinse or wipe with a suitable solvent, such as water, alcohol or the like, and optional ultrasonic cleaning. A polishing step might also be employed.

In one embodiment a plurality of resonators are fabricated upon a common substrate and the resonators are separated from each other after fabrication by suitable separation techniques, such as cutting or the like.

In a highly preferred embodiment in which the performance tuning material is deposited as a layer onto a surface of another material, the layer thickness preferably ranges up to about 10µ, and more preferably is about 0.005µ to about 5µ, and more preferably is about 0.1µ to about 1µ.

Although the above-described examples describe using a resonator without any modifications, the resonator can also be treated additionally with yet another "functionality" (a specialized coating) so that it is more sensitive to certain chemicals. The resonator may also be treated with a general coating to protect the resonator from corrosion or other problems that could impede its performance. The resonator can be coated with a selected material to change how the resonator is affected by a fluid composition. One option is a general coating for providing the resonator with additional properties such as corrosion resistance, chemical resistance, electrical resistance or a combination thereof. Another option, as noted above, is using a "functionality", which coats the tines with materials that are designed for a specific application, such as proteins or even monoclonal antibodies, to allow the resonator to be used as a pH meter, receptors, or immunoassay.

As will be appreciated, the coating or functionality can be applied onto the resonator using any known method, such as spraying or dipping. Further, the specific material selected for the coating or functionality will depend on the specific application in which the resonator is to be used. J. Hlavay and G. G. Guilbault described various coating and functionalization methods and materials to adapt piezoelectric crystal detectors for specific applications in "Applications of the Piezoelectric Crystal Detector in Analytical Chemistry," Analytical Chemistry, Vol. 49, No. 13, November 1977, p. 1890, incorporated herein by reference.

In yet another embodiment of the present invention, multiple mechanical resonators can be attached together in a single sensor to measure a wider range of responses for a given fluid composition. Multiple mechanical resonators can be included in a plurality of sensors, which are then assembled together for a particular system.

Though shorter duration lives are also possible for some applications, preferred resonators and sensors prepared according to the present invention exhibit the ability to consistently and reproducibly perform for extended periods of time, such as for at least 0.5 hours, more preferably at least 2 hours, still more preferably at least 6 hours, further still more preferably at least 12 hours and even still more preferably at least 24 hours. In some embodiments that resonators and sensors are capable of performing in their intended environment for at least 90 days, and even more preferably longer than 1 year and ideally for more than 5, 10 or 15 years. Thus, the present invention helps reduce the service needs of detection systems that employ the resonators and sensors of the present invention.

Resonators and sensors of the present invention are also unique in their ability to withstand, without compromise to performance, operating conditions that expose the resonator or sensor to one or a combination of acid (organic or inorganic), base (organic or inorganic), salt (e.g., NaCl), water, steam, crude oil, refined and unrefined hydrocarbon fluids, gasoline, synthetic and non-synthetic lubricants, hydraulic fluids, and greases, motor oil, ester oils, alcohols, varnish, soot, or high pressure flowing fluids. Preferably, the materials withstand the effects of these environments over a temperature range of −40° C. to about 170° C. for a period of at least 24 hours. In one highly preferred embodiment, the materials withstand the effects of these environments over a temperature range of −40° C. to about 170° C. for a period of at least 90 days, and more preferably at least one year, or more than 5, 10 and 15 years.

The preferred methods of the present invention contemplate providing a resonator that employs a performance tuning material and placing the resonator in a fluid (e.g., water, NaCl salt solution, rock salt brine, and $CaCl_2$, refined oil, unrefined oil, or otherwise). A signal is applied to the resonator and the response of the resonator to the signal is measured. In one particularly preferred embodiment, a variable frequency input signal is employed as described herein. Specific examples of preferred applications would be the employment of the resonators in accordance with the present invention as a sensor for a machine fluid pursuant to the teachings of U.S. Patent Application No. 60/419,404, (entitled "Machine Fluid Sensor and Method"; filed Oct. 18, 2002)(hereby incorporated by reference); or as an oilfield downhole tool deployed in a well bore for determining the properties of a fluid pursuant to the teachings of published U.S. Patent Application No. 20020178805 (hereby incorporated by reference), such as (without limitation) a property of a formation fluid sample including density, viscosity, dew point, bubble point, when a parameter of interest has leveled off, the onset of asphaltene precipitation, or the dielectric constant.

It will be further appreciated that functions or structures of a plurality of components or steps may be combined into a single component or step, or the functions or structures of one step or component may be split among plural steps or components. The present invention contemplates all of these combinations.

The manner of operating the resonators and sensors of the present invention may vary. In one embodiment, the sensor is operated continuously. In another, it may be intermittently operated. It is possible that the sensor may be operated only in preselected conditions, such as prior to starting vehicle operation, upon starting vehicle operation, during vehicle operation upon concluding vehicle operation, while the vehicle travels at a substantially constant velocity, while the vehicle accelerates or decelerates, or otherwise. Furthermore, the resonators and sensors of the present invention may be operated according to art-disclosed techniques network analyzers, see, e.g., U.S. Pat. No. 6,336,353 (Matsiev, et al.)("Method and apparatus for characterizing materials by using a mechanical resonator"); and U.S. Pat. No. 6,182, 499 (McFarland, et al.) and published U.S. Patent Application No. 20030000291, hereby incorporated by reference.

The resonators and sensors might operated with other components such as application specific integrated circuit (ASIC), such as is disclosed for example in commonly owned, co-pending application entitled "Integrated Measurement Assembly For A Machine Fluid Sensing System" (U.S. patent application Ser. No. 10/452,264), hereby incorporated by reference, as disclosed in commonly owned, co-pending application entitled "Application Specific Integrated Circuitry For Controlling Analysis Of A Fluid", claiming benefit of U.S. provisional application No. 60/419, 404), hereby incorporated by reference, as disclosed in co-owned, co-pending application entitled "Resonator Sensor Assembly" Ser. No. 10/804,379, PCT/US04/08531 and PCT/US04/08552, claiming benefit of U.S. provisional 60/456,517), as disclosed in co-owned, co-pending application entitled "Environmental Control System Fluid Sensing System And Method" (International patent application no. US03/32983) or as disclosed in co-owned, co-pending application entitled "Mechanical Resonators" PCT/US04/08526, claiming benefit of U.S. provisional application No. 60/452, 292). All of the foregoing are hereby incorporated by reference.

It should be understood that various alternatives to the embodiments of the invention described herein may be employed in practicing the invention. It is intended that the following claims define the scope of the invention and that the methods and apparatus within the scope of these claims and their equivalents be covered thereby. To the extent that the particular combinations of steps or materials covered by the following claims are not disclosed in the specification, the combinations of steps or materials are incorporated by reference into the specification.

What is claimed is:

1. A fluid sensor employing a mechanical resonator, comprising: a resonator portion adapted for resonating in a fluid under test; and an electrical connection between the resonator portion and a source of an input signal, including at least one electrode that is at least partially covered by a dielectric material; wherein the resonator portion, the electrical connection or both includes a base material and a performance-tuning material that is different from the base material, is relatively hydrophobic, and exhibits a porosity of less than about 5% of its volume.

2. A sensor according to claim 1, wherein the resonator portion includes at least one tine.

3. A sensor according to claim 2, wherein the resonator portion includes at least two tines.

4. A sensor according to claim 1, wherein the resonator portion includes at least two tines and the tines are joined together at a cross member to form a generally "H" shaped structure.

5. A sensor according to claim 3, wherein the base material of the resonator portion includes a piezoelectric material, an electrostrictive material, a magnetostrictive material, a piezoresistive material, an elasto-optic material, an anisotropic material, or combinations thereof and the electrical connection includes at least one electrode formed of a metal selected from gold, platinum, silver, chromium, aluminum, nickel, titanium or mixtures thereof.

6. A sensor according to claim 5, wherein the base material of the resonator portion includes quartz, lithium niobate, zinc oxide, lead zirconate titanate (PZT), a gallo-germanate, diomignite (lithium tetraborate), bismuth germanium oxide, gallium phosphate, gallium nitride, aluminum nitride or combinations thereof.

7. The sensor according to claim 6, wherein the performance-tuning material includes one or a combination of two or more materials selected from the group consisting of polytetrafluoroethylene, fluorosilicone, polyethylene, polypropylene, silicon carbide, silicon nitride, diamond, diamond-like carbon.

8. A sensor according to claim 5, wherein the performance-tuning material includes a material selected from the group consisting of polymers, ceramics, metals, metal carbides, metal nitrides, diamond, diamond-like carbon, and combinations thereof.

9. A sensor according to claim 6, wherein the performance-tuning material includes a material selected from the group consisting of polymers, ceramics, metals, metal carbides, metal nitrides, diamond, diamond-like carbon, and combinations thereof.

10. A sensor according to claim 8, wherein the performance tuning material: (i) includes a layer partially overlying a base resonator material; or (ii) includes a layer entirely overlying a base resonator material; or (iii) is an intermediate layer in the resonator; or (iv) is dispersed within a base material; or (v) includes any combination of (i), (ii), (iii) and (iv).

11. A fluid sensor employing a mechanical resonator, comprising: a resonator portion including at least two tines adapted for resonating in a fluid under test; and an electrical connection including at least one electrode formed of a metal selected from gold, platinum, silver, chromium, aluminum, nickel, titanium or mixtures thereof between the resonator portion and a source of an input signal, wherein the resonator portion includes: a doped or undoped base material that exhibits a dielectric constant that is substantially constant over a temperature range from at least about 0° C. to about 100° C., and is selected from the group consisting of quartz, lithium niobate, zinc oxide, lead zirconate titanate (PZT), gallo-germanates (e.g., Langasite ($La_3Ga_5SIO_{14}$), Langanite, or Langatate), diomignite (lithium tetraborate), bismuth germanium oxide, gallium phosphate, gallium nitride, aluminum nitride or combinations thereof; and a performance-tuning material that is relatively hydrophobic, exhibits a porosity of less than about 5% of its volume, is stable at about 150° C., is different from the base material and is selected from the group consisting of polymers, ceramics, metals, metal carbides or nitrides, diamond, diamond-like carbon, and combinations thereof.

12. The sensor according to claim 11, wherein the at least one electrode is at least partially covered by a dielectric material.

13. The sensor according to claim 12, wherein the base material is quartz.

14. The sensor according to claim 11, wherein the base material is lithium niobate.

15. The sensor according to claim 11, wherein the base material is PZT.

16. The sensor according to claim 11, wherein the base material is a gallo-germanate.

17. The sensor according to claim 11, wherein the performance-tuning material includes one or a combination of two or more materials selected from the group consisting of fluoropolymers, silicones, silanes, polyolefins, carbides, nitrides, oxides, diamond, diamond-like carbon, and combinations thereof.

18. The sensor according to claim 11, wherein the performance-tuning material includes one or a combination of two or more materials selected from the group consisting of polytetrafluoroethylene, fluorosilicone, polyethylene, polypropylene, silicon carbide, silicon nitride, diamond, diamond-like carbon.

19. The sensor according to claim 11, wherein the performance-tuning material includes a fluoropolymer.

20. The sensor according to claim 11, wherein the performance-tuning material includes a ceramic.

21. The sensor according to claim 11, wherein the performance-tuning material includes a metal nitride.

22. The sensor according to claim 11, wherein the resonator portion formed from a wafer.

23. The sensor according to claim 12, wherein the performance-tuning material is a layer that is continuous or intermittent, along edges of the resonator base material, within the interior of the resonator base material, or a combination thereof.

24. A method for making a resonator, comprising: a) forming a plurality of resonators on a common substrate; the resonators including: a resonator portion adapted for resonating in a fluid; and an electrical connection including at least one electrode formed of a metal selected from gold, platinum, silver, chromium, aluminum, nickel, titanium or mixtures thereof between the resonator portion and a source of an input signal, wherein the resonator portion includes: a doped or undoped base material that exhibits a dielectric constant that is substantially constant over a temperature range from at least about 0° C. to about 100° C., and is selected from quartz, lithium niobate, zinc oxide, lead zirconate titanate (PZT), gallo-germanates, diomignite (lithium tetraborate), bismuth germanium oxide, gallium phosphate, gallium nitride, aluminum nitride or combinations thereof; and a performance-tuning material that is different from the base material and is selected from the group consisting of polymers, ceramics, metals, metal carbides or nitrides, diamond, diamond-like carbon, and combinations thereof; and b) separating the resonators from each other.

25. The method according to claim 24, further comprising: c) at least partially covering at least one electrode with a dielectric.

26. The method according to claim 25, wherein the performance tuning material is resistant to absorption of oils.

* * * * *